(12) United States Patent
Biary

(10) Patent No.: US 8,026,717 B1
(45) Date of Patent: Sep. 27, 2011

(54) WALL STUD DETECTOR AND MAGNET

(76) Inventor: Sohail Biary, Simi Valley, CA (US)

( * ) Notice: Subject to any disclaimer, the term of this patent is extended or adjusted under 35 U.S.C. 154(b) by 368 days.

(21) Appl. No.: 12/317,390

(22) Filed: Dec. 22, 2008

Related U.S. Application Data

(60) Provisional application No. 61/009,019, filed on Dec. 20, 2007.

(51) Int. Cl.
*G01N 27/72* (2006.01)
(52) U.S. Cl. ....................................... 324/228
(58) Field of Classification Search .................. None
See application file for complete search history.

(56) References Cited

U.S. PATENT DOCUMENTS

| | | | | |
|---|---|---|---|---|
| 4,013,291 A | * | 3/1977 | Brass et al. | 273/239 |
| 4,671,255 A | * | 6/1987 | Dubrul et al. | 128/899 |
| 5,055,188 A | * | 10/1991 | Johnston et al. | 210/222 |
| 6,229,294 B1 | * | 5/2001 | Wun | 324/67 |
| 6,696,827 B2 | * | 2/2004 | Fazekas et al. | 324/67 |
| 6,747,536 B1 | * | 6/2004 | Miller, Jr. | 335/285 |
| 7,161,343 B1 | * | 1/2007 | Biary | 324/67 |
| 7,690,124 B1 | * | 4/2010 | Henry | 33/286 |

FOREIGN PATENT DOCUMENTS

EP 416162 A1 * 3/1991

* cited by examiner

*Primary Examiner* — Paresh Patel
(74) *Attorney, Agent, or Firm* — Colin P. Abrahams

(57) ABSTRACT

A wall stud detector comprises a housing having a surface for moving over a substrate and a recess in the surface extending into the housing. A target associated with the housing comprises an outer casing and a magnet located in the outer casing. The outer casing comprises a central enclosure for the magnet and an outer peripheral portion. The outer peripheral portion of the target is spaced from the outer peripheral portion of an adjacent target when the target and the adjacent target are stacked with respect to each other.

23 Claims, 15 Drawing Sheets

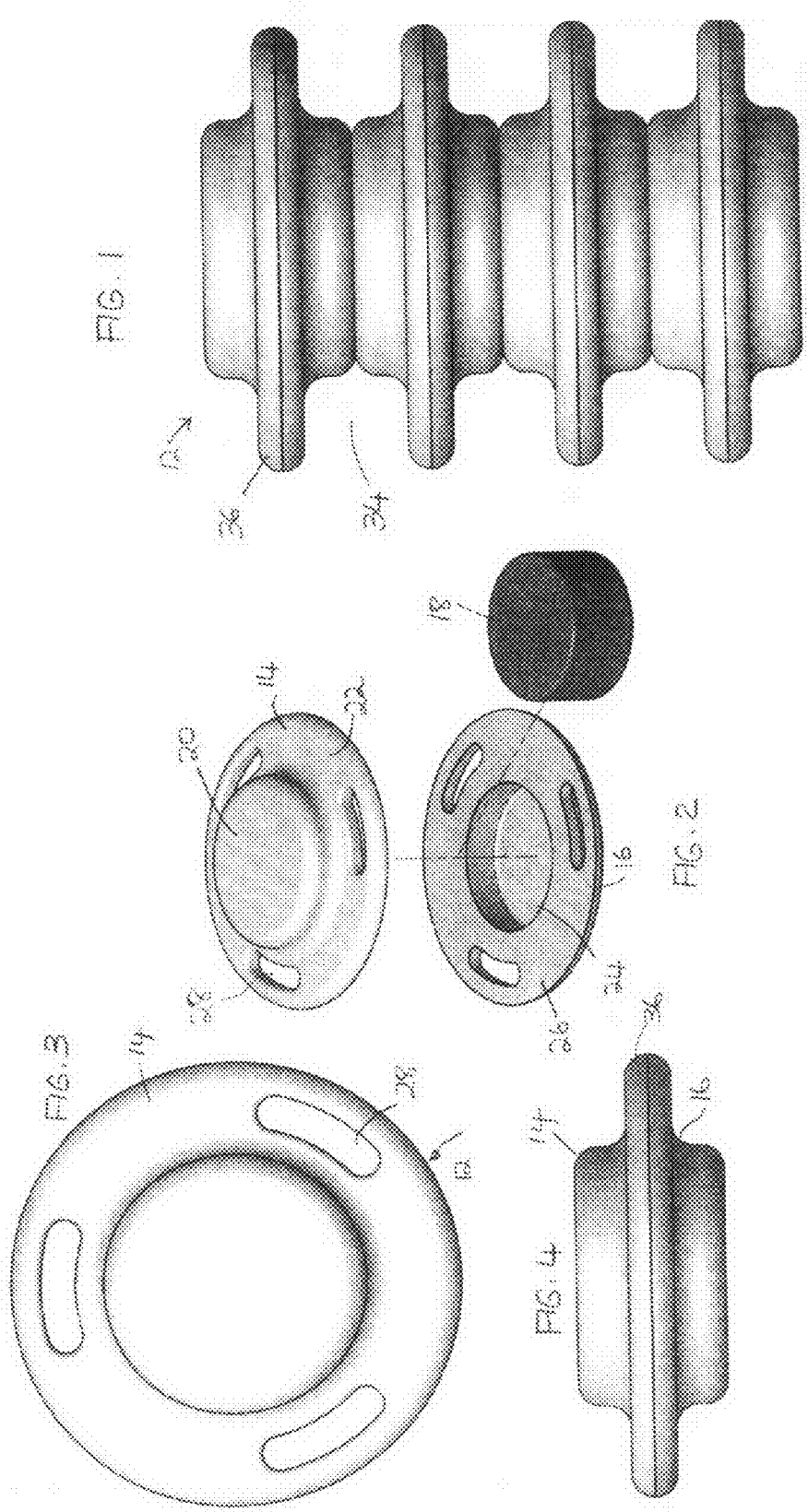

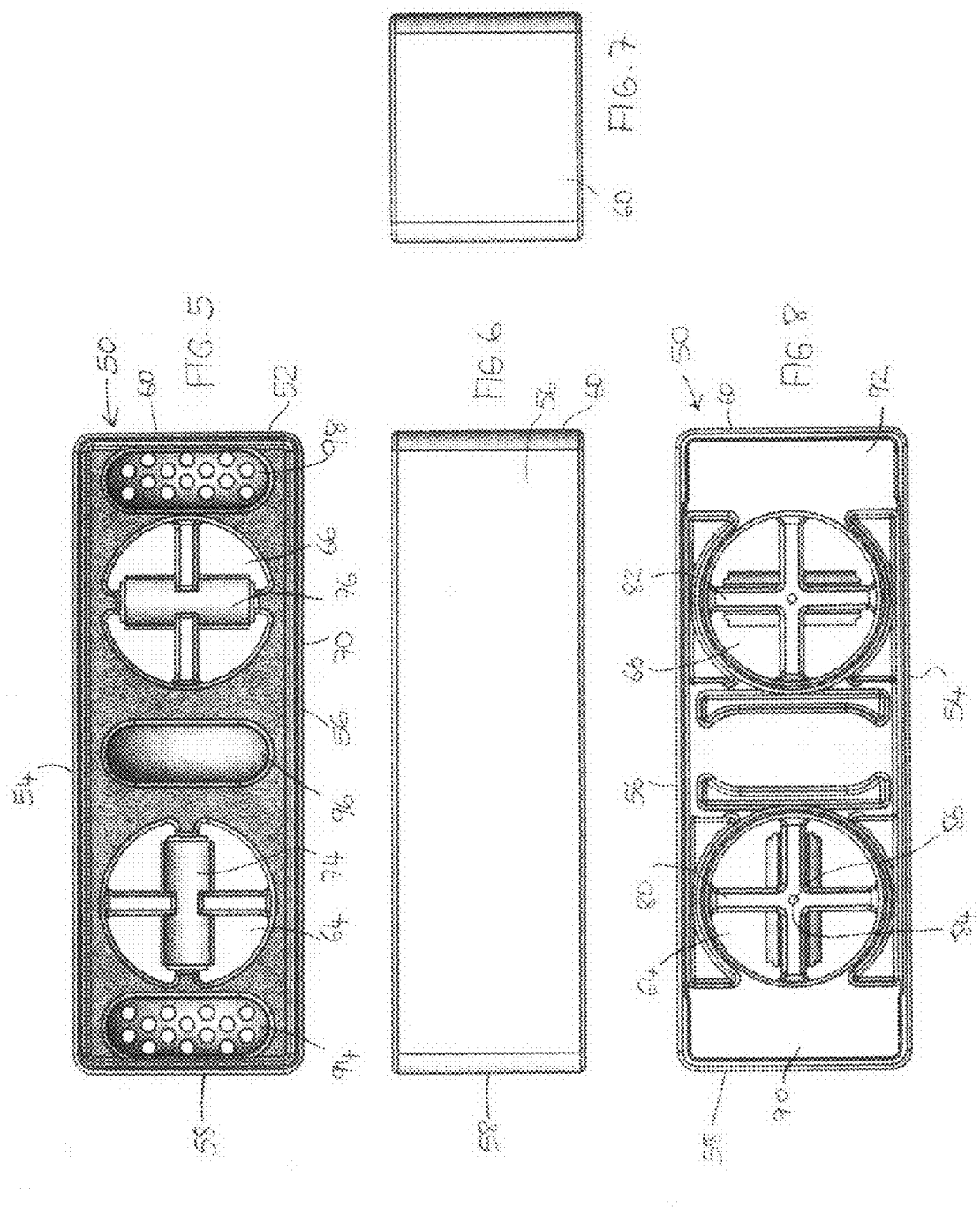

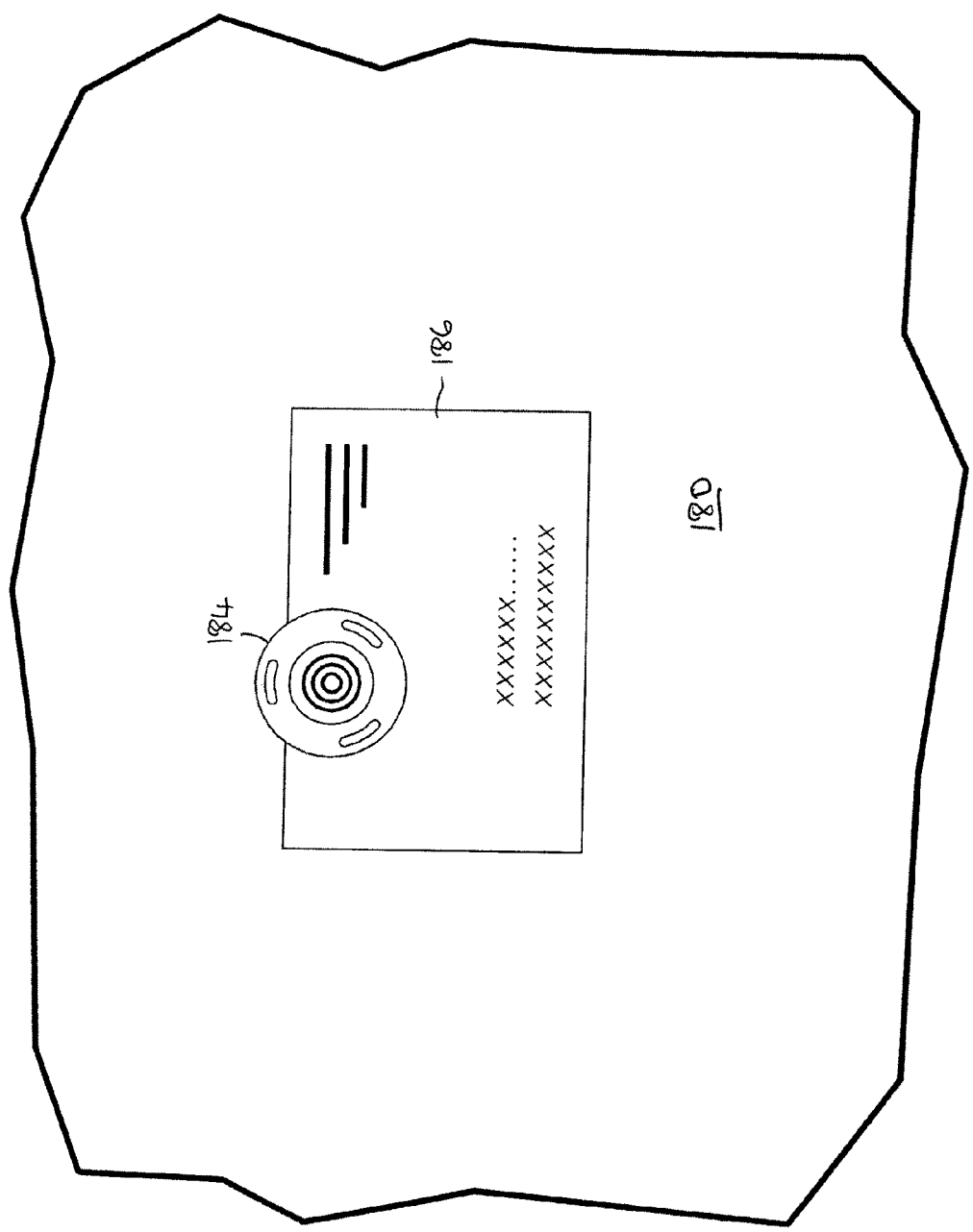

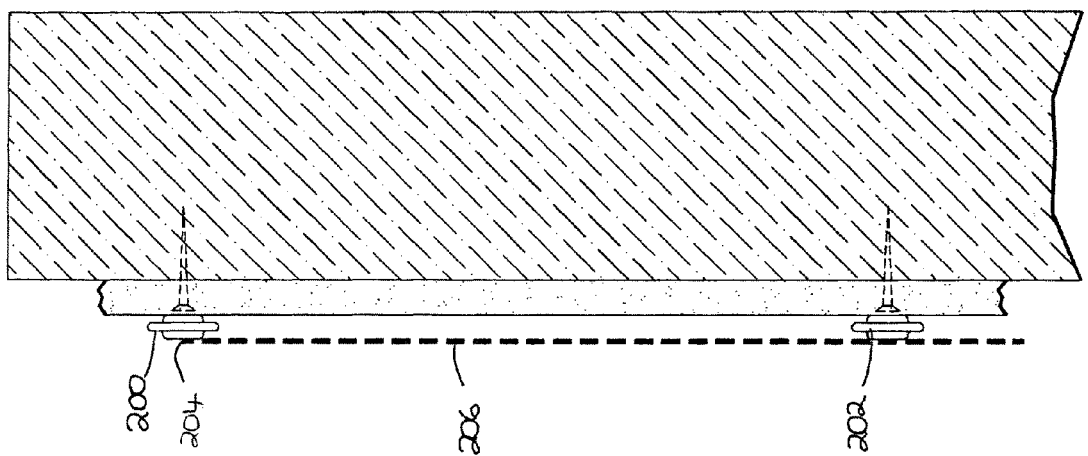
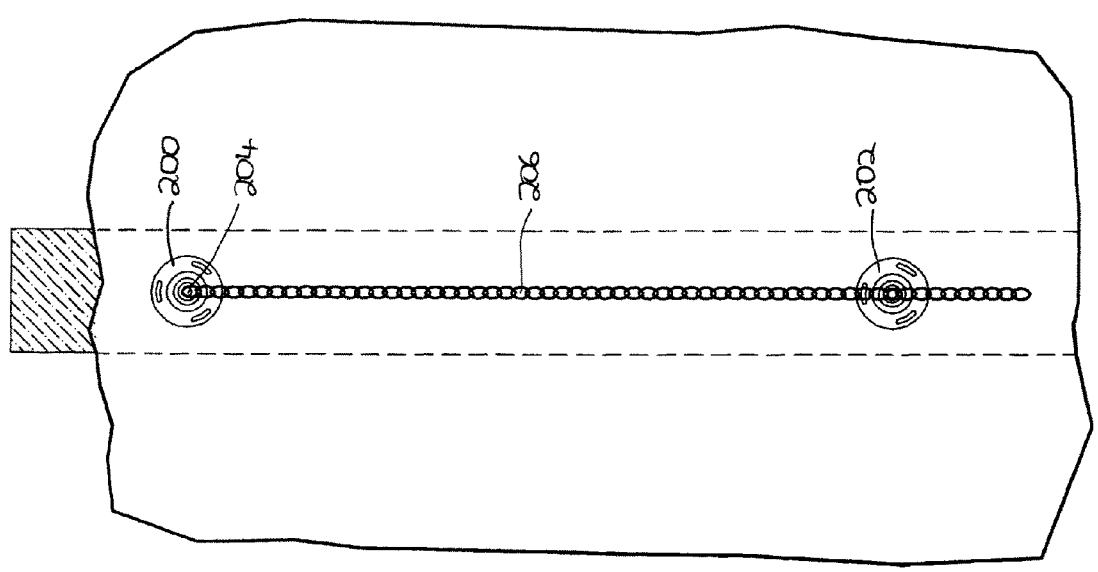
FIG. 18(a)
FIG. 18(b)

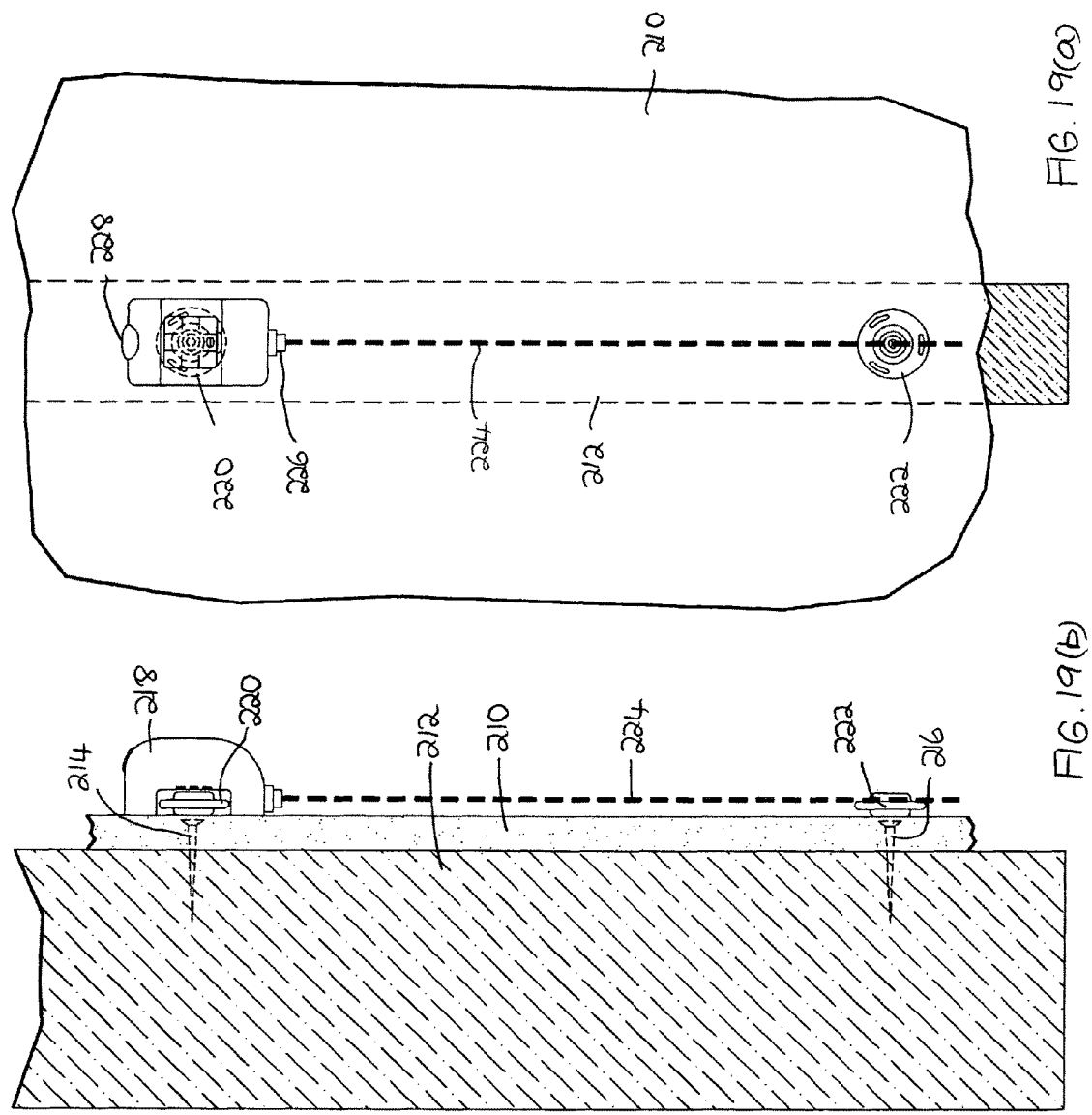

WALL STUD DETECTOR AND MAGNET

CROSS REFERENCE TO RELATED APPLICATIONS

This application claims the benefit of U.S. Provisional Patent Application No. 61/009,019 filed Dec. 20, 2007 and is incorporated herein by reference in its entirety.

FIELD AND BACKGROUND OF THE INVENTION

This invention relates generally to a wall stud detector and magnet. The wall stud detector and magnet may operate as a locator and marker for metal studs in walls or beams or the like. More specifically, the invention is directed towards a device which can be used on a wall or other relevant surface, and which can, through the use of magnets, identify and locate metal objects, such as screws, nails, tacks or the like, in the wall which are used to secure wooden beams in the framing of walls and other structures. Further, the invention relates to magnetic markers which can be magnetically held on a wall at an area of a nail, screw or the like, for the purposes of marking a spot, or securing an object to the wall. Such an object will typically comprise relatively light objects such as paper, photographs or the like. However, where stronger magnets are used, this may facilitate the ability for the wall stud locator and marker of the invention to hold heavier objects. Such heavier objects may include, but are not limited to, chains, lights, levels and the like.

SUMMARY OF THE INVENTION

According to one aspect of the invention, there is provided a wall stud detector comprising: a housing having a surface for moving over a substrate and a recess in the surface extending into the housing; and a target comprising an outer casing and a magnet located in the outer casing, the outer casing comprising a central enclosure for the magnet and an outer peripheral portion, the outer peripheral portion of the target being spaced from the outer peripheral portion of an adjacent target when the target and the adjacent target are stacked with respect to each other.

Preferably, the target has an upper component and a lower component, the upper component having a cup shaped portion and a disc shaped portion extending outwardly from the cup shaped portion, the lower component having a cup shaped portion and a disc shaped portion extending outwardly from the cup shaped portion, the cup shaped portion of the upper component being adjacent the cup shaped portion of the lower component so as to form the central enclosure, and the disc shaped portion of the upper component and the disc shaped portion of the lower component forming the peripheral portion.

In one embodiment, the peripheral portion of the target has at least one aperture formed therein, preferably in the form of a slot. Further, the target may have a projection thereon for connecting an object to the target. A hook member may be provided for receipt within the aperture in the peripheral portion, the hook member further comprising a fastening portion for holding an object.

Preferably, the central enclosure has a thickness approximately three times the thickness of the peripheral portion. The target may be generally of circular shape and the peripheral portion extends outwardly from the approximate center of the central enclosure, the peripheral portion having a diameter approximately twice the diameter of the central enclosure.

In one embodiment, the recess in the surface of the housing is configured so that a target contained in the recess will remain in the recess when magnetically attracted to a stud in the wall. In a different embodiment, the recess in the surface of the housing is configured so that a target contained in the recess will be discharged from the recess and the housing when magnetically attracted to a stud in the wall. The housing may further comprise a small metal holder which magnetically attracts the target when the target is in the recess to keep the target from falling out of the recess.

In one form, the wall stud detector further comprises levels for identifying the vertical and horizontal orientation of the housing, and a laser beam source, a power source for the laser beam source and a switch for activating and deactivating the laser beam source.

In one embodiment, the housing further comprises a small metal holder which magnetically attracts the target when the target is in the recess to keep the target from falling out of the recess, and the housing is configured so that a target contained in the recess will remain in the recess when magnetically attracted to a stud in the wall.

Preferably, at least one storage compartment is located in the housing for storing targets. The storage compartment has a door at an access opening to the storage compartment to open and close access to the storage compartment.

The wall stud detector may further comprise a chain or plumb line which can be suspended from the target when magnetically attracted to a stud in the wall.

In one embodiment, the recess is dimensioned so that the target can move therein between a first position in which the target is stored in the recess and a second position in which the target is magnetically attracted to a stud in the wall, the target making a striking sound as it strikes the substrate when moving from the first position to the second position, thereby alerting the user that a stud has been located.

A target container for holding and storing a plurality of targets may be provided. The target container may comprise a tubular member having an open end for receiving and dispensing targets, the open end having a flange adjacent thereto, the flange being dimensioned so as to receive the outer peripheral portion of the target thereunder so that the targets are received and dispensed into the target container approximately normal to the axis of the container.

According to another aspect of the invention, there is provided a target for use with a wall stud detector, the target comprising an outer casing and a magnet located in the outer casing, the outer casing comprising a central enclosure for the magnet and an outer peripheral portion, the outer peripheral portion of the target being spaced from the outer peripheral portion of an adjacent target when the target and the adjacent target are stacked with respect to each other.

According to the invention, there is provided a device for identifying and locating the position of metal objects behind or in a wall using a magnet, and dispensing a magnet on the wall so that it will remain on the wall through magnetic attraction to the metal object.

Preferably, the device of the invention comprises a housing which carries the magnet in a releasable manner, the housing being especially adapted to slide over a wall and discharge the magnet from the housing when a metal object is detected or attracts the magnet in the housing, the discharged magnet being held on the wall at the area of the metal object by virtue of the magnetic force therebetween.

Further, in accordance with the invention, there is provided a device including a storage container for a storing plurality of magnets, whereby the magnets can be removed from the storage container when needed and placed in the housing for attachment to the wall, and thereafter replaced back in the storage container after use.

In accordance with another aspect of the invention, there is provided a magnet for use with a wall stud detector, the magnet being configured and shaped for easy handling. Often, magnets used in this context may have a fairly strong magnetic force, making them difficult to separate from each other and also raising the possibility of pinching the user when the magnet is adjacent another magnet or a metal object. The magnet in accordance with the invention may have a central portion and a ringed at least partially outer portion so that spaces are created between the magnet and other objects to which the magnet is attached. The spaces so created will make it easier to grasp and handle the magnet and also prevent or reduce any pinching caused by the magnet.

Detecting metal objects in the framework of a wall, or studs behind a wall, is well-known, and many different types of devices have been developed for this purpose. Typically, in a popular method of building construction, a house, office or other type of structure is framed using vertical, horizontal and sometimes diagonally located wooden beams, all attached to each other to form a sturdy frame for supporting an outer and in inner wall. These wooden framing members are typically connected to each other with screws or nails at predetermined intervals, according to a specific pattern. Once the frame has been constructed, sheet material comprising the walls is placed thereover, and the frame, as well as the screws, nails and other hardware material, is completely hidden from view.

It sometimes becomes necessary to determine exactly where the frame or wood beams are positioned behind a wall. This may be necessary for the purposes of securing heavy objects to the wall, since it is desirable to place a screw, plug or other attachment mechanism directly into the wooden frame, as opposed to merely the sheet wall, which often lacks the requisite strength for supporting heavy objects. As such, different stud locators have been developed for this purpose. Of course, finding a stud or nail in the frame identifies the position of the frame itself, hence the need to locate such studs.

In one aspect, the present invention provides a mechanism not only for determining the precise location of a frame member behind the wall, by magnetically locating metal objects used to construct the frame, but also provides markers which can be attached to the wall, the markers being in the form of magnets. These markers have many functions, including locating a metal object and holding its identified position for later use, or just attaching in a releasable manner objects, such as photographs, notes, or many other types objects to the wall. Of course, the nature of the object which can be held against the wall in accordance with the invention will typically be lighter, but increased weight can be supported depending upon the strength of the magnets which may be used, as well as the precise location and size of the metal objects within the wooden frame.

Preferably, the present invention is constructed so that a small metal object is placed in the housing near the surface for keeping a magnet to be dispensed in position on the surface prior to discharge thereof. The small metal object is preferably selected so that it is large enough to keep the magnet in the housing but will not otherwise interfere with the location of a stud and the discharge of a magnet from the housing, as will be described.

A magnet is preferably located for dispensing on the surface of the housing. The magnet preferably has a substantially non-scratching covering over at least a portion of its surface. Further, a plurality of magnets may be provided, and at least some of the magnets may be color-coded.

Preferably, the stud detector and magnet for locating and marking a stud further comprises a storage container, the storage container being adapted to contain a plurality of magnets which can be removed therefrom and placed on the surface or other portion of the housing. The storage container may generally be of tubular shape, and may comprise a cover movable between an open position wherein magnets can be accessed, and a closed position where the magnets are sealed therein. In one embodiment, the cover of the storage container contains a small magnetic object therein, wherein opening of the cover has the effect of moving the small magnetic object so as to dispense a magnet adjacent the cover within the container.

Preferably, spacer members are provided to suitably space the housing from the wall surface or substrate. The spacer members may be covered, at least in part, with a non-scratching or non-abrasive material, so as to prevent or reduce scratching or damage by the housing to the substrate. The spacer members may comprise an elongate projection along each edge of the housing extending beyond the surface, the elongate projections forming an open channel therebetween. Alternatively, the spacer members may comprise a plurality of legs on the housing extending beyond the surface, the legs defining an open channel therebetween.

The stud detector for locating and marking studs in a wall may also comprise a storage area for a pencil or other writing material or implement, as well as a slot or other guide mechanism whereby the pencil can be used in association with the locating and marking device to mark on the wall with a dot or other symbol the location at which a metal fastener has been detected. The housing itself may be comprised of a transparent, or partially transparent material, to help the user in determining exactly where a metal fastener, or a wooden beam, is located, so that an opaque housing does not obstruct or cover the detected stud position.

In addition, magnets of different size and strengths may be provided. For example, a stronger magnet may be used for the purposes of detecting and establishing the presence and location of a metal fastener in a wall. Once this has been found, a magnet of lesser strength can be used to replace the magnet of stronger force since it can already be seen where the metal fastener or stud is located. This is useful where a user desires to find a number of metal markers or fasteners in a wall, and these can be quickly located with a stronger magnet, but identified on a more permanent basis with a smaller magnet or one of lesser strength. For marking purposes, many or some of the magnets may be color-coded, or have other markings or graphics thereon. Further, the surface of the magnet may be treated at some point to enable the user to write on the magnet. The writing may be permanent, or such that it can be easily erased or washed off. Marking the magnet with written information may be useful for certain projects in order to provide guidance as to what should be installed or mounted at a particular point where the fastener or wood beam has been found. The magnets may also be shaped differently or have varying profiles or surface texture to achieve the same purpose.

The wall stud detector of the invention may also come as a kit, comprising the stud detector for locating a stud and marking its position, as well as the storage container for magnets. These may, in some way, be attachable to each other so that they can be stored without becoming separated from each other and/or lost. In one preferred form, if the storage container and housing are attached to each other, the method of attachment is one which allows these parts to be released from each other while the housing is operating to locate magnetic fasteners, and then subsequently reattached for the purposes of storing the device as a whole or a unit.

BRIEF DESCRIPTION OF THE DRAWINGS

In the drawings:

FIG. 1 shows a series of magnets in accordance with the invention in stacked formation;

FIG. 2 shows a break open view of the magnet in accordance with the invention;

FIG. 3 shows a top view of the magnet in accordance with the invention;

FIG. 4 shows a side of a single magnet in accordance with the present invention;

FIG. 5 shows a top view of a housing for a magnet in accordance with the present invention;

FIG. 6 shows a side of the housing as shown in FIG. 5 of the drawings;

FIG. 7 is an end view of the housing shown in FIG. 5 of the drawings;

FIG. 8 is a bottom view of the housing shown in FIG. 5 of the drawings;

FIGS. 15 and 16 show a note or card being held in position by a target of the invention, FIG. 16 being a detail of FIG. 15;

FIGS. 18(a) and 18(b) are front and side views of the wall with targets attached thereto;

FIGS. 19(a) and 19(b) show a target holder in accordance with the invention including a laser beam.

DETAILED DESCRIPTION OF THE INVENTION

Figure 9A:
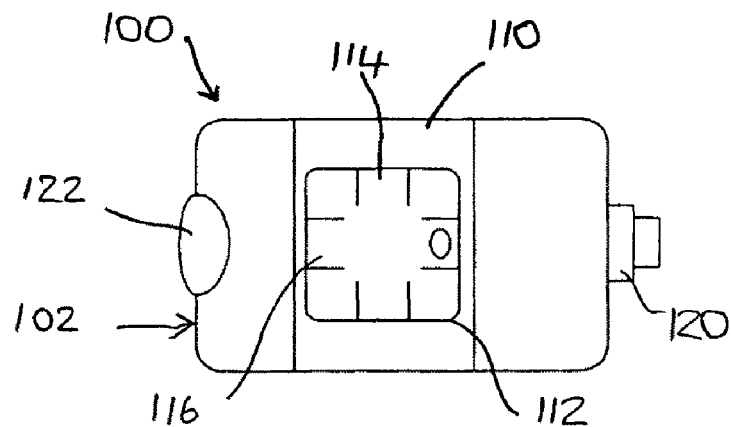
FIGS. 9(a), 9(b) and 9(c) are a top and side views respectively of a stud detector and magnet, including a level and laser beam.

With reference to FIG. 1 of the drawings, there is shown in stacked formation four targets 12 in side view. From FIG. 2 of the drawings, it will be seen that each target 12 comprises an upper cover 14, a lower cover 16, and a magnet 18. The upper cover 14 has a central cavity 20, and, a circular rim 22. The lower cover 16 has a central cavity 24 and a circular rim 26. In each of the rims 22 and 26, there are formed three elongate slots 28.

In use, the magnet 18 is placed in the cavity 24 of lower cover 16, and the upper cover 16 is placed over the lower cover 16 so that the magnet 18 is also contained within the cavity 20. The two cavities 20 and 24 join to form a closed housing for the magnet 18. The rims 22 and 26 overlie and correspond with each other, and the slots 28 in the upper cover 14 register with the slots in the lower cover 16. The upper cover 14 and lower cover 16 are fastened together, such as by welding, glue or any other means that will ensure that they remain fixed together, and the magnet 18 is snugly accommodated within the housing formed by the cavities 20 and 24.

FIG. 3 of the drawings shows a top view of the target 12, while FIG. 4 shows a side view of a single target 12.

It will be seen from FIG. 1 that, when a stack of targets 12 are placed one above the other, a space 34 is formed between the ring 36 of one target 12, and the ring 36 of an adjacent target 12. The space 34 is sufficiently large so that the user's finger can be inserted in the space 34 to pry targets 12 apart from each other, when in the stacked position. The shape and configuration of the target 12 illustrated in FIGS. 1 to 4 of the drawings thus facilitate their comfortable handling, making it easier to grasp them and reducing the potential for pinching of the user's skin, which may occur between magnets not so constructed, especially magnets which have stronger magnetic forces.

FIGS. 5 to 8 show various views of a target holder 50 in accordance with one aspect of the present invention. The target holder 50 comprises a target housing 52 having side walls 54 and 56, and end walls 58 and 60.

As will be seen in FIG. 5 of the drawings, which is a top view of the target holder 50, the target holder 50 has a first channel 64 and a second channel 66. Near the top side 70 of the target holder 50, and in the channels 64 and 66, there are two levels 74 and 76 respectively. The level 74 formed in the channel 64 is a aligned with the longitudinal axis of the target holder, while the level 76 formed in the channel 66 is at a 90 degree angle relative to the level 74. The orientation of the levels 74 and 76 thus provides the user with level indications in both the vertical and horizontal planes.

In FIG. 8 there is shown a bottom view of the target holder 50, and each of the channels 64 and 66 has therein a cross piece 80 and 82. The cross pieces 80 and 82 have at the approximate center thereof an aperture 84, and formed in the aperture there is a small metal holder 86, embedded in the aperture 84 so as to be retained therein.

On each side of the target holder 50, there is a soft material 90, so that when the target holder 50 slides over a wall or other substrate surface, it will not scratch or mark such surface.

In FIG. 5 of the drawings, it will be seen that the target holder 50 has three storage areas 94, 96 and 98, which are able to receive and hold targets 12, of the type seen, for example, in FIGS. 1 to 4 of the drawings, so that additional targets 12 can be conveniently stored within the target holder 50 until they are needed.

In use, targets 12 are inserted in the first channel 64 and/or second channel 66. The position of the cross piece 80 or 82 is such that the target 12 will be fully received in the channel 64, and not project outwardly from the channel 64, in its ready-to-apply position. The metal holder 86 will be magnetically attracted to the magnet within the target 12, and this will have the effect of maintaining the target 12 within the channel 64 until needed.

Figure 9B:
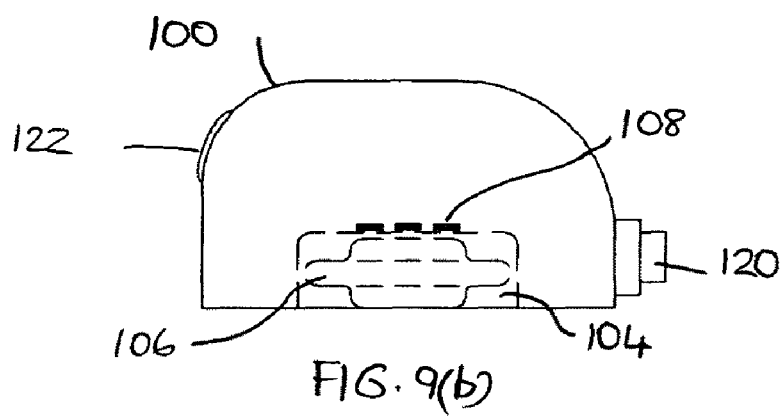
Figure 9C:
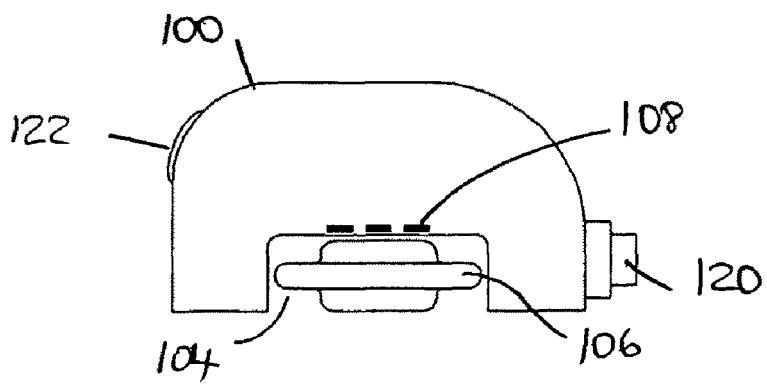

With reference to FIGS. 9(a), 9(b) and 9(c) of the drawings, there is shown a target holder 100 in accordance with another aspect of the invention. The target holder 100 in FIG. 9(a) shows a top view, including a housing 102, and the recess 104 in the housing 102 for receiving a target 106. The target 106 may be configured in a manner described with respect to FIGS. 1 to 4 of the drawings. In the top portion of the recess 104, there may be one or more metal holders 108, and three as shown in FIGS. 9(b) and 9(c), which engage the magnet in the target 106 so as to keep it within the recess 104.

On the top surface 110 of the target holder 100, there is provided a level assembly 112, comprising levels 114 and 116, at right angles to each other so as to provide the user with indications of level in both the vertical and the horizontal planes.

The target holder 100 further comprises a laser light 120, operated by a switch 122. The target holder 100 can be placed in the level position with respect to the vertical and horizontal planes, as determined by the level assembly 112, and in this position, the laser 120 activated or switched on by the switch 122, so as to provide a beam of light in the desired direction. This will assist the user in any task which requires such a guide light to identify a horizontal or vertical (or other) plane.

In use, the target holder 100 with the target 106 may be moved over a substrate with studs therein, such as a framed wall. When a metal stud is detected in the wall, the target 106 will become magnetically attached to this metal stud. The target 106 will thus be held against the substrate, and will hold the target holder 100 with it when it is in the recess. Thus, the target 106 forms the link or connector between the stud in the wall and the metal holder 108, so as to keep the target holder 100 temporarily affixed to the substrate. The target holder itself can be rotated and moved until in the desired vertical and horizontal orientation, and the laser 120 may then be switched on using switch 122, so as to provide a beam of light, as required by the user.

Figure 10A:
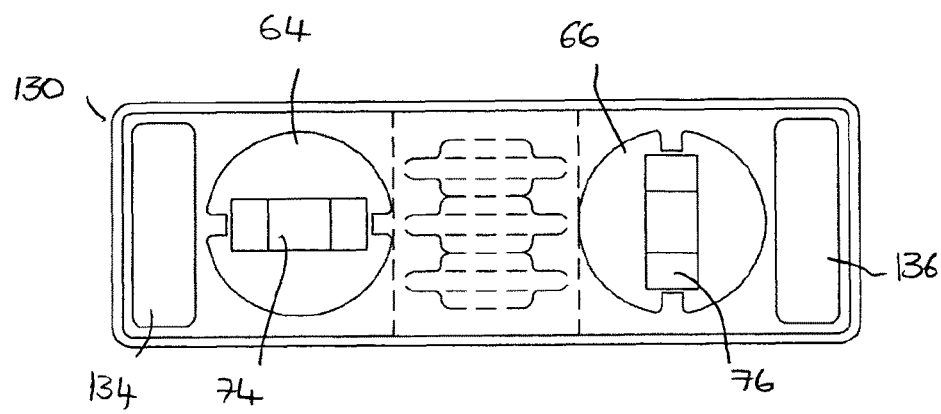
FIGS. 10(a) and 10(b) are top and bottom views of a target holder in accordance with another aspect of the invention.
Figure 10B:
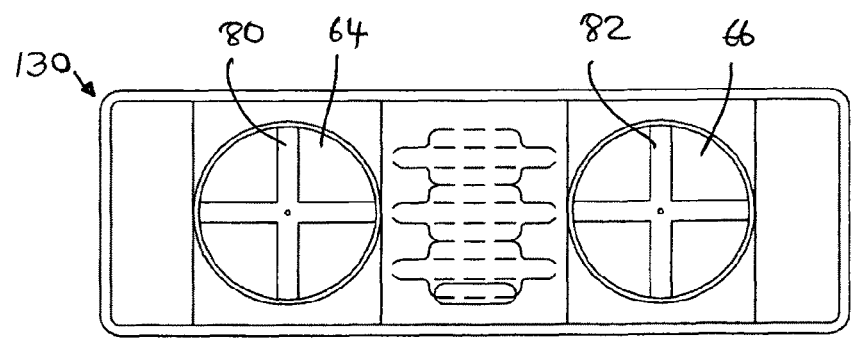

In FIGS. 10(a) and 10(b) of the drawings, there is shown top and bottom views respectively of a target in accordance with another embodiment of the invention. Where feasible, similar reference numerals for corresponding parts have been used in these Figures, as were used in FIGS. 5 to 8. It will be seen that the target holder 130 in FIGS. 10(a) and 10(b) has a central storage compartment 132 in which is located three targets 134. This is in addition to the lateral compartments 134 and 136 which may also be used for storage purposes.

Figure 11B:
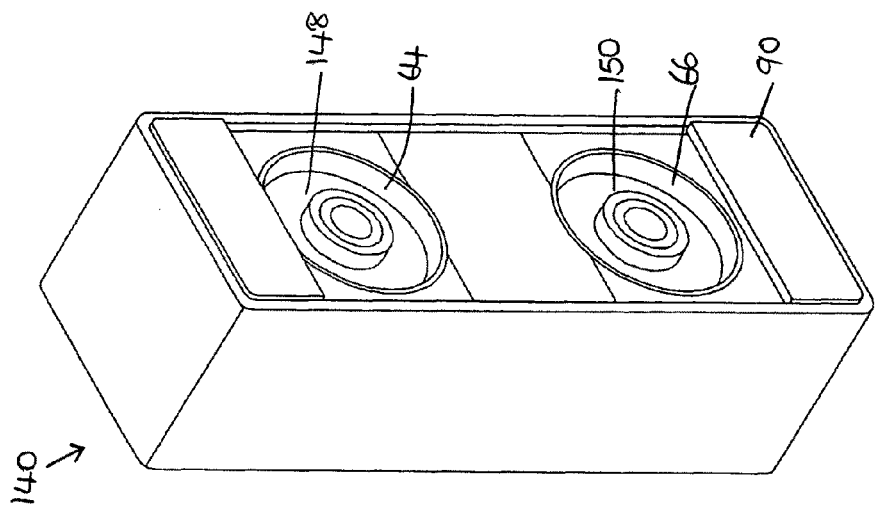
FIGS. 11(a) and 11(b) are perspective views of a target holder in accordance with a further embodiment of the invention.
Figure 11A:
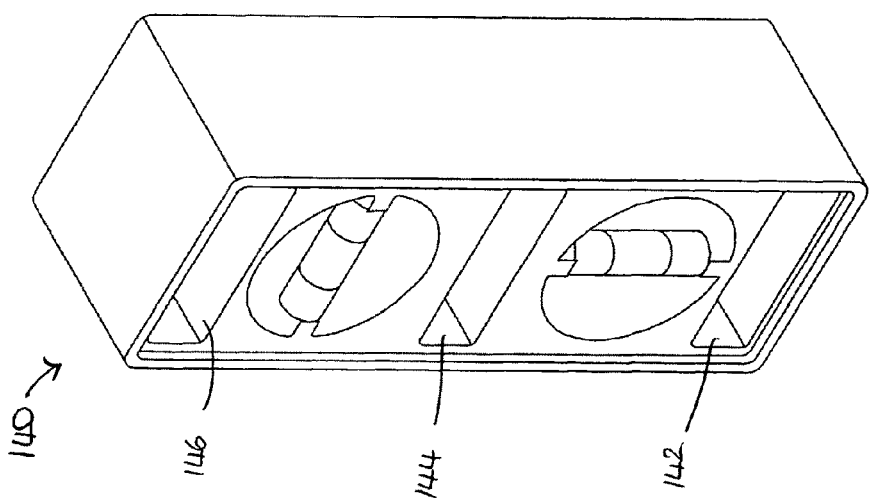
Figure 12A:
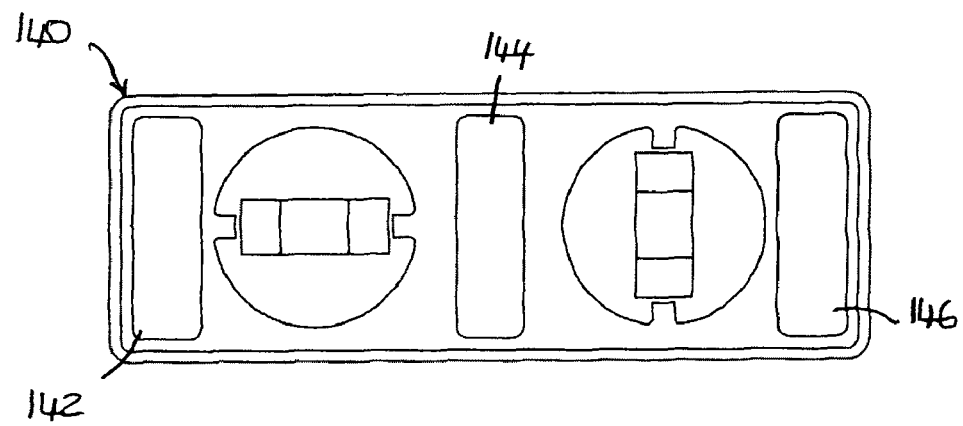
FIGS. 12(a) and 12(b) are front and rear views of the target holder shown in FIGS. 11(a) and 11(b) of the drawings.
Figure 12B:
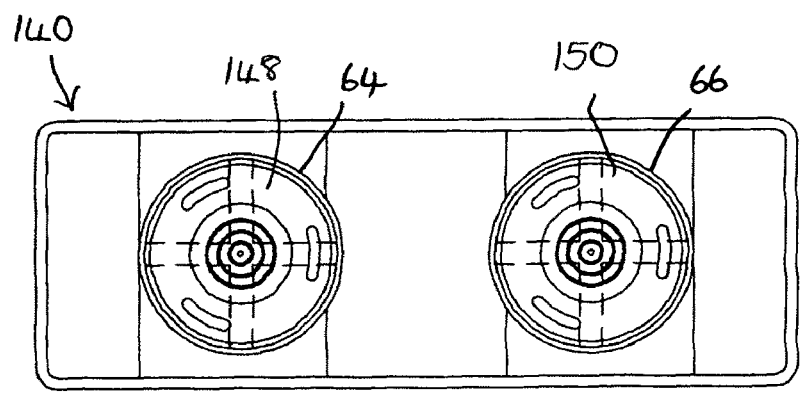

With reference to FIGS. 11(a) and 11(b) of the drawings, FIG. 11(a) shows a front perspective view, and FIG. 11(b) shows a bottom perspective view, of a target holder 140 in accordance with the invention. FIG. 11(a) shows three storage areas 142, 144 and 146 for targets to be stored, in addition to those which are positioned in the channels 64 and 66. FIG. 11(b) shows targets 148 and 150, located in the channels. Further, FIG. 11(b) also shows clearly the soft material 90 placed on the target holder to prevent scratching of damage to the substrate over which it is moved.

Figure 13C:
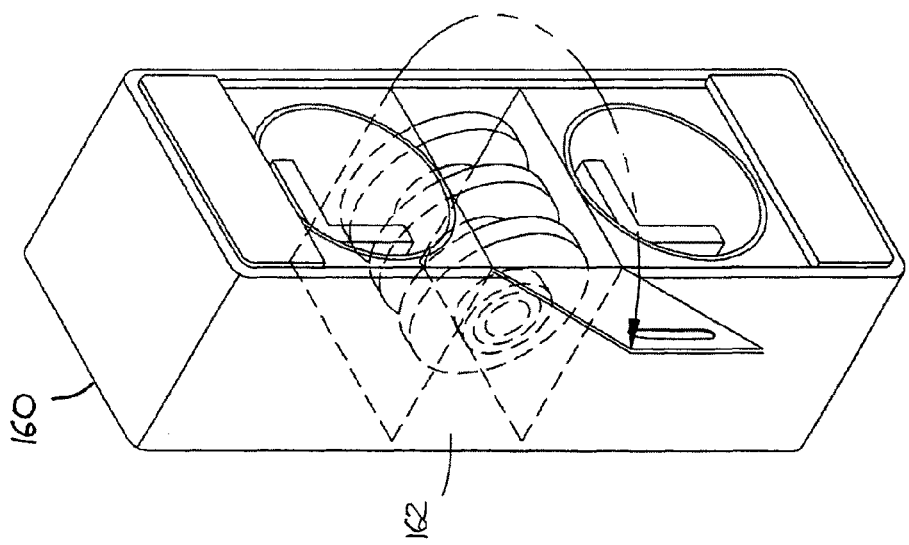
FIGS. 13(a), 13(b) and 13(c) are front and rear perspective views of a target holder with target in accordance with a further aspect of the invention.
Figure 13B:
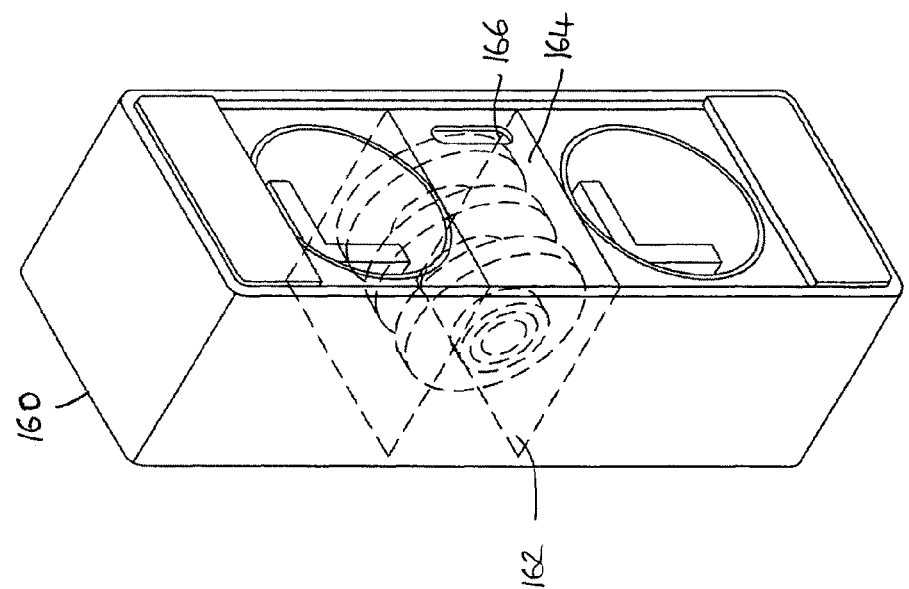
Figure 13A:
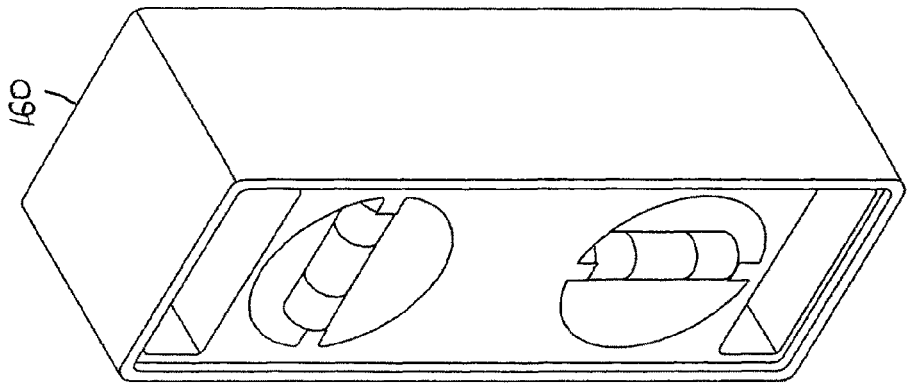

In FIG. 13(a) of the drawings, there is shown a front perspective view of a target holder 160 in accordance with one aspect of the present invention. FIGS. 13(b) and 13(c) show the bottom perspective view of the target holder 160, including a target storage area 162. The target storage area 162 has on one side thereof a door 164 with a small slot 166 in the door, in order to conveniently open and close it. FIG. 13(b) shows the door 164 in the closed position, while FIG. 13(c) shows the same door 164 in the open position, providing access to the stored targets 168, which may be placed within the storage area 162.

Figure 14:
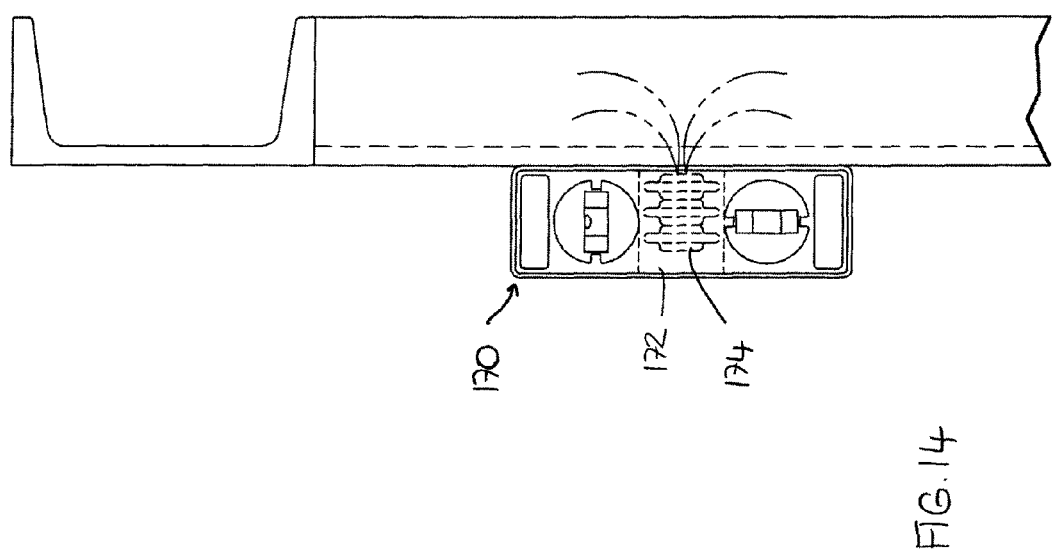
FIG. 14 of the drawings shows a target holder of the invention, when placed on a wall or substrate.

With reference to FIG. 14 of the drawings, there is shown a target holder 170 including a compartment 172 containing three targets 174.

Figure 15:
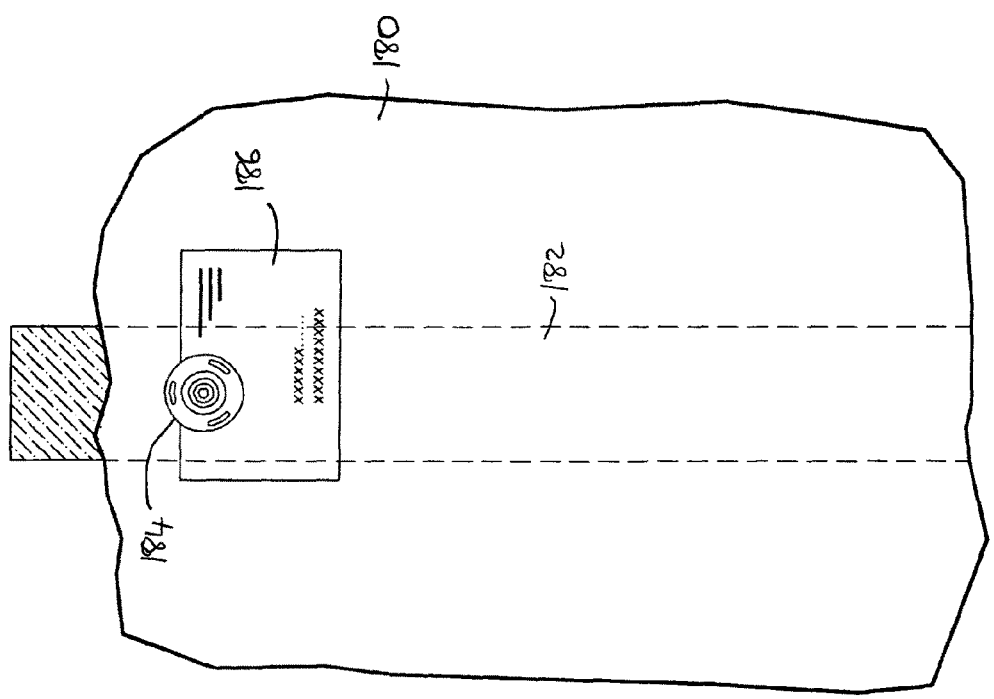

With reference to FIG. 15 of the drawings, there is shown a wall 180 which is fixed on a frame 182. A stud (not shown) has been located in the frame 182, and a target 184 magnetically affixed to the wall 180 by virtue of the magnetic attraction between the magnet in the target 184 and the stud in the wall 180. A card, note or other material 186 is pinned to the wall 180 between the target 184 and the wall 180, offering a temporary note or reminder or display of the note 186 as desired by the user.

Figure 17A:
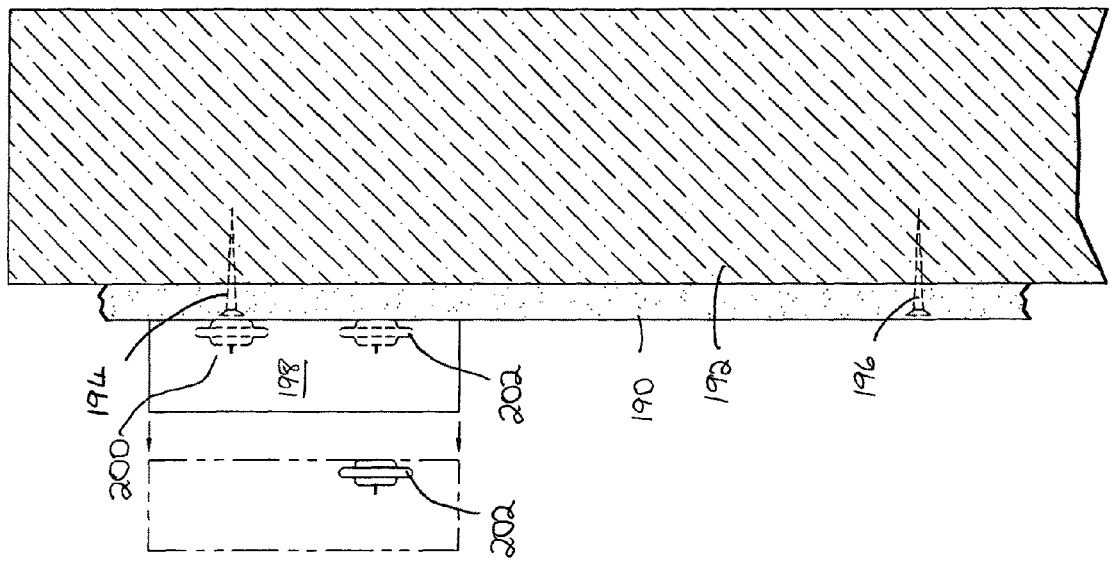
FIGS. 17(a) and 17(b) are front and side views respectively of a target holder with target on a wall.
Figure 17B:
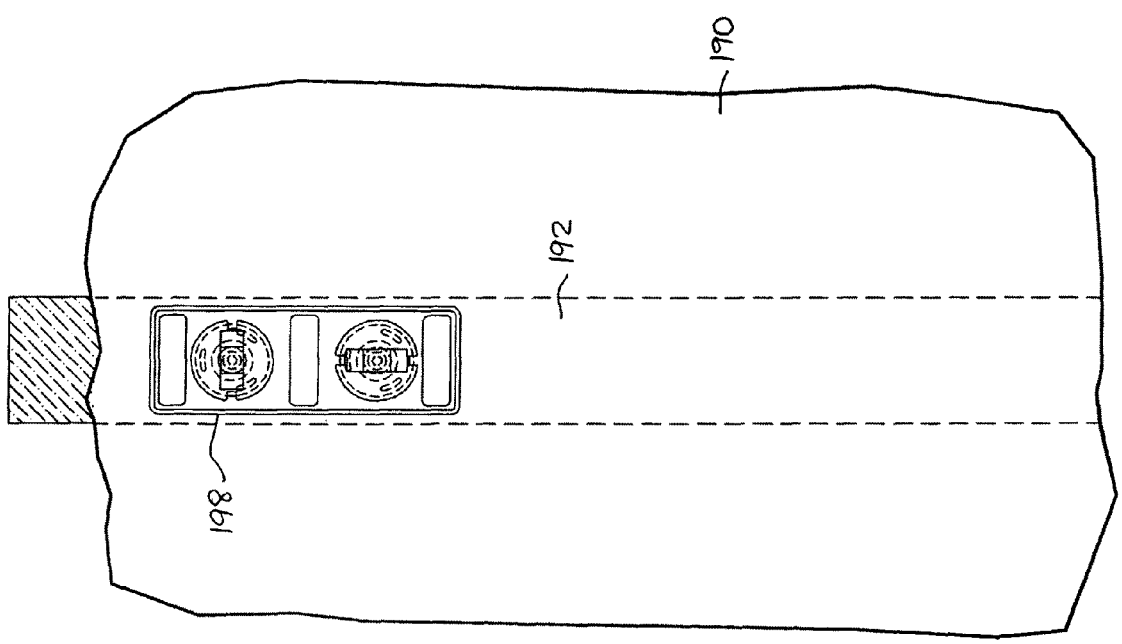

With reference to FIGS. 17 and 18 of the drawings, there is shown a wall sheet 190 attached to a wooden beam 192 by means of nails 194 and 196. In FIGS. 17(a) and 17(b), the target holder 198 is moved up and down the wall, and a target 200 is dispensed at nail 194, and another target 202 dispensed at nail 196 when the target holder 198 is moved down the wooden beam 192. As shown in FIGS. 18(a) and 18(b) of the drawings, the targets 200 and 202 have small projections 204, and a chain 206 is attached to the projection 204 on the target 200, as well as that on the target 202. The chain 206, which may hang freely, such as a plumb line, from target 200 will be attached to both targets 200 and 202, provides information as to the vertical plane though which the nails 194 and 196 are located.

With reference to FIGS. 19(a) and 19(b) of the drawings, there is shown a wall 210 affixed to a wooden beam 212 by means of nails 214 and 216. A target holder 218, similar in construction and form to that shown in FIGS. 9(a), 9(b) and 9(c) of the drawings, locates the nails 214 and 216 respectively, at which point targets 220 and 222 are magnetically attracted. The target 220, as seen in FIGS. 19(a) and 19(b), holds the target holder 218 against the wall 210. The target holder 218 has a level so that its horizontal and vertical position can be adjusted. When in the desired position, a laser beam 224 is directed from a laser source 226, the laser beam 224 being switched on and off by switch 228. In this embodiment, therefore, a light beam is used to identify a vertical or horizontal plane through which the nail 214 passes.

It will be seen that the target 220 in these FIGS. 19(a) and 19(b), as well as all the other figures, includes the slots as described with respect to FIGS. 1 to 4 of the drawings. The slots can be used to attach items, either by string, hooks or other connection mechanisms so that such items may be attached or suspended from the target 220. Thus, the target 220 may itself be a holder of a large variety of items and objects which are directly threaded to the slots, or have a hook attached to both the slot and the object.

Figure 20A:
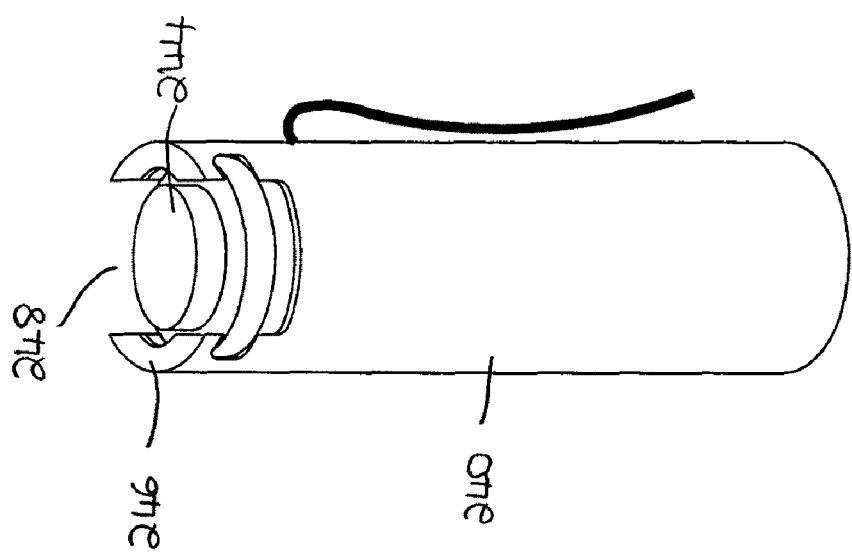
FIGS. 20(a) and 20(b) is a perspective view and a cross-sectional view respectively through a target container in accordance with the invention.
Figure 20B:
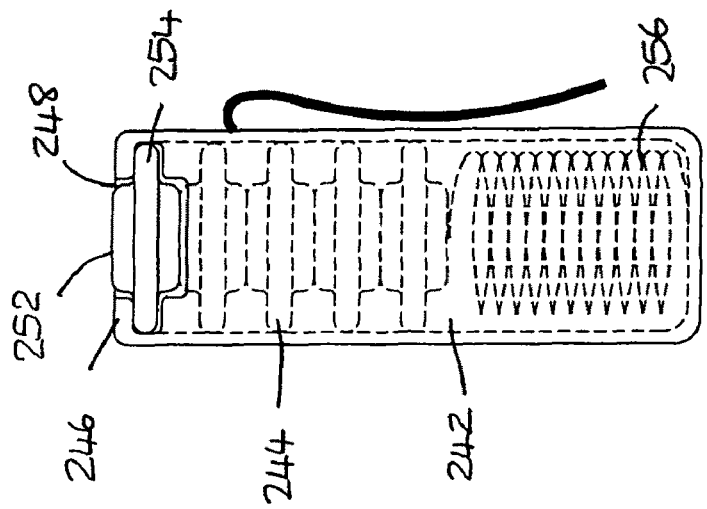

With reference to FIGS. 20(a) and 20(b) of the drawings, there is shown a container 240, generally cylindrical in shape. The container 240 defines therein a space 242 having a diameter just slightly larger than the targets. A series of targets 244 are located within the container 240. The upper end 246 of the container 240 has an opening 248, the opening 248 being bordered by a flange 250. The opening 248 is slightly larger than the diameter of the housing 252 of the target, but smaller than the outer diameter of the ring 254. As best seen in FIG. 20(a) of the drawings, a target 244 is slid into the container 240 at the top, such that the ring 244 is below the flanges. In this way, it will be received in the container 240. Additional targets are inserted in the container by pushing the top target down, and inserting the next target in a similar manner. A spring 256 is formed in the container, and urges the targets upwardly so that they can be easily ready for dispensing in a reverse mechanism to that in which they are inserted.

The stud detector of the invention, as illustrated in the drawings, thus generally consists of a holder and one or more magnetic targets. One purpose of the holder is to sustain or hold the magnetic target inside one or more of the cavities formed in the holder, which are designed to be of round or square or rectangular shape. Each of the cavities may be closed on all sides or open from one side or multiple sides and when the target or targets are loaded in the holder, they can be hidden or visible from outside.

When the holder surface is in contact with a holder base there is a specific space which is created between the target and the substrate, which will typically be a wall or dry wall sheet rock, or wood panel. At the point of attraction with any metal object in the substrate, the target will start to move out of the cavity in the holder toward the metal object in the substrate and this movement will create a mechanical sound of hitting the metal or other object and then coming back to the original location in the cavity once the sweeping motion takes the holder away from metal object.

The holder can have a triggering mechanism with a power source and a visual colored or plain light or a mechanical indicator and/or sound buzzer to indicate the target disengaging or engaging the holder at the point of being attracted to the metal object.

One or more sides of an outer frame of the housing can have a point with a hole in it to be used as plumb bob or it may have a laser pointing device or a self leveling pointer. The target may have a magnet with a protective outer shell constituted from some form of plastic or polymer or rubber or the like. The target can be round or square or rectangle. The target can be of any size. Further, the target can be any weight.

The target can have a recessed or thinner outer ring or flange, or portion thereof, that is substantially thinner than the center portion thickness of the target. This will create a convenient space between adjacent magnets or targets which are stacked or mounted on a surface so that an object or a finger is readily able to pry the target apart from an adjacent target or other object. It has the effect of creating a holding surface to hold the target.

The target may have one or more holes of selected shape in the outer ring or a recessed groove. The target may have a light or a laser pointing device or a level mounted on it or it can use paper or other material to have writing or instructions printed on it. In another embodiment, it can be made of glow-in-the-dark material, or coated with a some substance that can have such effect.

The target preferably has a multipurpose use, such as for fridges and any magnetic surfaces. The shape of the target will help to have a good grip to remove it easily from magnetic surfaces.

In accordance with the invention, there is provide a magnet or target for use with a housing wherein the magnet has a central portion which is thicker than the periphery thereof so form spaces between stacked magnets. This facilitates separating the magnets without the magnets pinching.

The peripheral portion has one or more holes for, for example, string or twine, which can be tied thereto to suspend objects from the magnet.

The invention is not limited to the precise details, but many variations may be made within the scope of the invention. The housing may be of any suitable shape, and may have recesses or handles to facilitate the user holding the housing and moving it over a wall. Instead of the continuous legs 40 and 42, there may just be four cylindrical (or other shaped) legs at each corner, or along the lower surface. This would serve the purpose of keeping the magnets held close to the wall, but allow movement of the housing not only in one plane, but in the horizontal and vertical plane as well, since the discharge magnet would be able to pass through passages nearly all around the housing.

The invention claimed is:

1. A wall stud detector comprising:
   a housing having a surface for moving over a substrate and a recess in the surface extending into the housing;
   a target comprising an outer casing and a magnet located in the outer casing, the outer casing comprising a central enclosure for the magnet and an outer peripheral portion, the outer peripheral portion of the target being spaced from the outer peripheral portion of an adjacent target when the target and the adjacent target are stacked with respect to each other.

2. A wall stud detector as claimed in claim 1 wherein the target has an upper component and a lower component, the upper component having a cup shaped portion and a disc shaped portion extending outwardly from the cup shaped portion, the lower component having a cup shaped portion and a disc shaped portion extending outwardly from the cup shaped portion, the cup shaped portion of the upper component being adjacent the cup shaped portion of the lower component so as to form the central enclosure, and the disc shaped portion of the upper component and the disc shaped portion of the lower component forming the peripheral portion.

3. A wall stud detector as claimed in claim 1 wherein the peripheral portion of the target has at least one aperture formed therein.

4. A wall stud detector as claimed in claim 3 wherein the aperture is a slot and three slots are formed in the peripheral portion.

5. A wall stud detector as claimed in claim 1 wherein the target has a projection thereon for connecting an object to the target.

6. A wall stud detector as claimed in claim 3 further comprising a hook member for receipt within the aperture in the peripheral portion, the hook member further comprising a fastening portion for holding an object.

7. A wall stud detector as claimed in claim 1 wherein the central enclosure has a thickness approximately three times the thickness of the peripheral portion.

8. A wall stud detector as claimed in claim 1 wherein the target is generally of circular shape and the peripheral portion extends outwardly from the approximate center of the central enclosure, the peripheral portion having a diameter approximately twice the diameter of the central enclosure.

9. A wall stud detector as claimed in claim 1 wherein the recess in the surface of the housing is configured so that a target contained in the recess will remain in the recess when magnetically attracted to a stud in the wall.

10. A wall stud detector as claimed in claim 1 wherein the recess in the surface of the housing is configured so that a target contained in the recess will be discharged from the recess and the housing when magnetically attracted to a stud in the wall.

11. A wall stud detector as claimed in claim 1 wherein the housing further comprises a small metal holder which magnetically attracts the target when the target is in the recess to keep the target from falling out of the recess.

12. A wall stud detector as claimed in claim 1 further comprising levels for identifying the vertical and horizontal orientation of the housing.

13. A wall stud detector as claimed in claim 1 further comprising a laser beam source, a power source for the laser beam source and a switch for activating and deactivating the laser beam source.

14. A wall stud detector as claimed in claim 13 wherein the housing further comprises a small metal holder which magnetically attracts the target when the target is in the recess to keep the target from falling out of the recess, and the housing is configured so that a target contained in the recess will remain in the recess when magnetically attracted to a stud in the wall.

15. A wall stud detector as claimed in claim 1 further comprising at least one storage compartment in the housing for storing targets.

16. A wall stud detector as claimed in claim 15 wherein the storage compartment has a door at an access opening to the storage compartment to open and close access to the storage compartment.

17. A wall stud detector as claimed in claim 1 further comprising a soft fabric on the surface of the housing to prevent or reduce marking or other damage to the substrate.

18. A wall stud detector as claimed in claim 1 further comprising a chain or plumb line which can be suspended from the target when magnetically attracted to a stud in the wall.

19. A wall stud detector as claimed in claim 9 wherein the recess is dimensioned so that the target can move therein between a first position in which the target is stored in the recess and a second position in which the target is magnetically attracted to a stud in the wall, the target making a striking sound as it strikes the substrate when moving from the first position to the second position, thereby alerting the user that a stud has been located.

20. A wall stud detector as claimed in claim 1 wherein the target is configured to remain on the substrate and to hold an object between the target and the substrate.

21. A wall stud detector as claimed in claim 1 further comprising a target container for holding and storing a plurality of targets.

22. A wall stud detector as claimed in claim 21 wherein the target container comprises a tubular member having an open end for receiving and dispensing targets, the open end having a flange adjacent thereto, the flange being dimensioned so as to receive the outer peripheral portion of the target thereunder so that the targets are received and dispensed into the target container approximately normal to the axis of the container.

23. A target for use with a wall stud detector, the target comprising an outer casing and a magnet located in the outer casing, the outer casing comprising a central enclosure for the magnet and an outer peripheral portion, the outer peripheral portion of the target being spaced from the outer peripheral portion of an adjacent target when the target and the adjacent target are stacked with respect to each other.

* * * * *